United States Patent [19]

Bredeweg

[11] 4,050,995
[45] Sept. 27, 1977

[54] METHOD FOR DETERMINING WATER VAPOR TRANSMISSION RATE OR WATER CONTENT

[75] Inventor: Roger L. Bredeweg, Midland, Mich.

[73] Assignee: The Dow Chemical Company, Midland, Mich.

[21] Appl. No.: 358,576

[22] Filed: May 9, 1973

Related U.S. Application Data

[62] Division of Ser. No. 11,557, Feb. 1, 1971, Pat. No. 3,886,057.

[51] Int. Cl.² ............................................. G01N 27/46
[52] U.S. Cl. ................................ 204/1 T; 204/195 W; 250/282; 73/29.76; 73/336.5
[58] Field of Search ..................... 204/1 T, 195 W; 250/281–283

[56] References Cited

U.S. PATENT DOCUMENTS

| 3,072,556 | 1/1963 | Czuha | 204/195 W |
|---|---|---|---|
| 3,188,283 | 6/1965 | Cole | 204/195 W |
| 3,367,850 | 2/1968 | Johnson | 204/1 T |
| 3,546,449 | 12/1970 | Aspinal | 250/283 |
| 3,661,724 | 5/1972 | Strickler | 204/195 W |
| 3,712,860 | 1/1973 | Gabrusenok | 204/195 W |

FOREIGN PATENT DOCUMENTS 1,176,507   1/1970   United Kingdom ........... 204/195 W

OTHER PUBLICATIONS

Keidel, "Anal. Chem.", vol. 31, No. 12, Dec. 1959, pp. 2043–2048.

*Primary Examiner*—T. Tung
*Attorney, Agent, or Firm*—Arthur J. Young

[57] ABSTRACT

A cell for absorbing and electrolyzing the water vapor transmitted from a sample used in an apparatus for rapidly determining the water vapor transmission rate through plastic films or like structures and water content in solid, liquid and gaseous materials wherein electrolysis of the water vapor from a test sample takes place in a cell electrolysis assembly comprising a first electrode support and a first electrode and a second electrode support and a second electrode with a foraminous matrix having an electrically conductive water absorption material therein disposed electrically between the first and second electrodes. The water vapor transmission rate or water content of the sample can be rapidly and accurately determined by quantitative mass spectrometer calculations of the oxygen and hydrogen generated during electrolysis or by calculation of the electrical current needed to electrolyze the water vapor which are related with primary accuracy.

4 Claims, 7 Drawing Figures

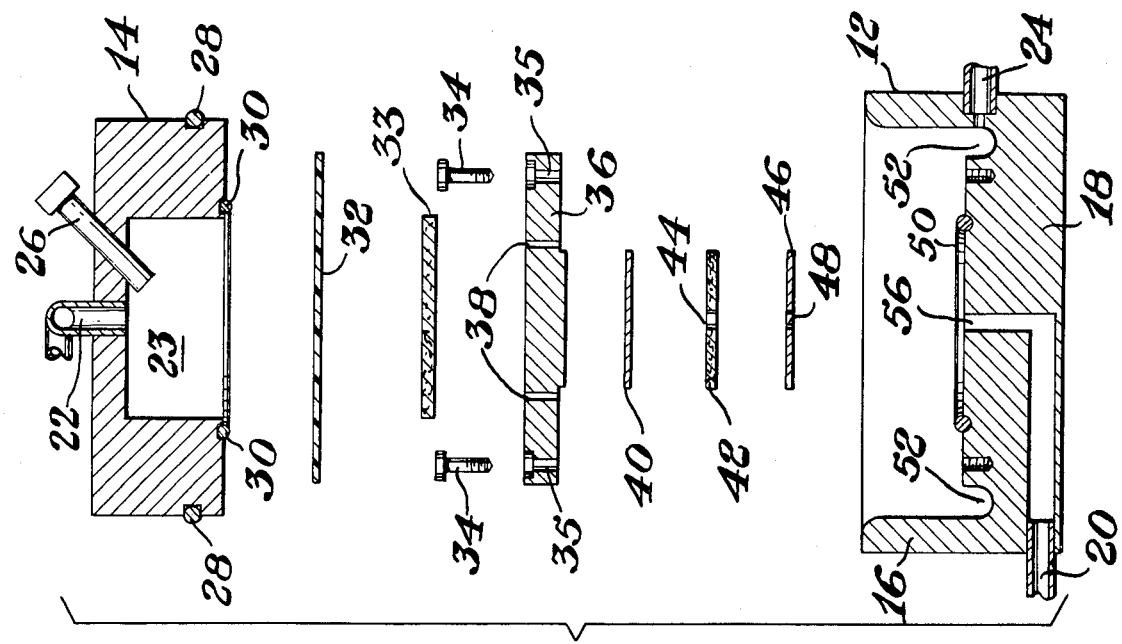
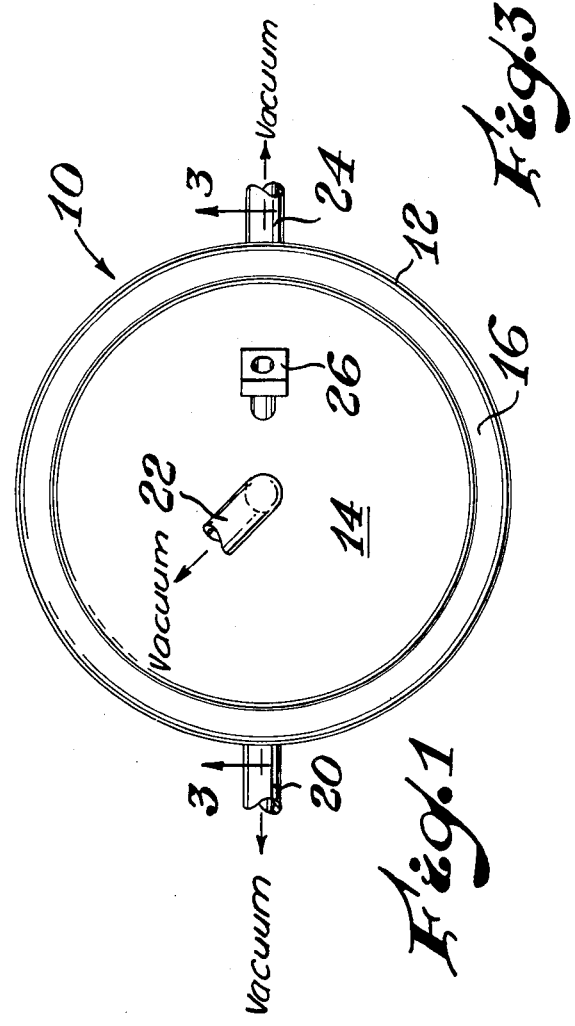
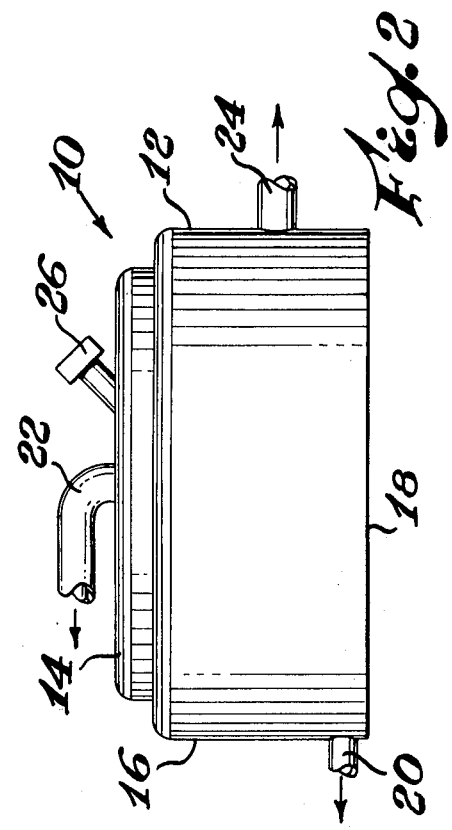

METHOD FOR DETERMINING WATER VAPOR TRANSMISSION RATE OR WATER CONTENT

CROSS REFERENCE TO RELATED APPLICATION

This is a division of application Ser. No. 111,557 filed Feb. 1, 1971, now U. S. Pat. No. 3,886,057.

BACKGROUND OF THE INVENTION

1. Field of the Invention

This invention relates to an apparatus for measuring the water vapor transmission rate through plastic films or like structure which can also be used for measuring water content of solid, liquid and gaseous materials, with particular reference to a cell used in said apparatus for rapidly absorbing and electrolyzing the water vapor transmitted from a test sample.

2. Description of the Prior Art

In general, there are many known devices employing a variety of principles for determining the water vapor transmission rate through plastic films or like structure which may also be useful for measuring the water content of solid, liquid and gaseous materials.

The simplest device used is a standard metal cup having an opening with a definite area. The cup is partially filled with a desiccant which will reduce the relative humidity in the cup to ten percent when a sample to be tested is secured over the opening. The cup and sample are weighed and placed in an oven set at a specific temperature, usually 100° F. The oven is also maintained at a specific relative humidity, usually 100 percent. After several days the cup is removed from the oven and weighed. The water vapor transmission rate, hereinafter referred to as W.V.T.R., is then calculated in units of grams of water permeating the test material per hundred square inches of sample per 24 hour period.

A second device employs a cell having a moisture sensitive crystal wherein the resistance to an electrical current passing through the crystal is proportional to the humidity surround the crystal. The relative humidity on one side of the sample to be tested in usually fixed at one hundred percent and the relative humidity on the other side is set at 10 percent. Again, the temperature is normally maintained at 100° F. The time needed for an incremental increase in humidity, normally 1 percent, is then obtained from the calibrated change in current passing through the crystal. The cycle is repeated until a relatively constant time is established from which the W.V.T.R. is calculated.

A third device incorporates a cell which works on the same principle as the present invention but is of a distinctly different design. This type of cell and principle are illustrated in *Analytical Chemistry*, Vol. 21, No. 12, pp. 2043–2048 (December 1959 ). The principle employed by the illustrated cell provides for the absorption and electrolysis of the water vapor that permeates through a test sample which has 100 percent relative humidity on one side and zero percent on the other. The W.V.T.R. is calculated from the electrical current required to electrolyze the absorbed water vapor which are related with primary accuracy.

The major problem with known devices and methods for measuring W.V.T.R. through plastic films or like structures is an inability to make rapid uncomplicated tests with accurate reproducible results. Sensitive calibrations, slow response and high experimental errors result in steady state rate calculations which may not reproduce. Even though the transmission rate of most gases such as oxygen, nitrogen and carbon dioxide through plastic films can be easily and rapidly measured, the transmission of water vapor is an exception. Water is a highly polar molecule which clings to most surfaces, thus causing water vapor to transport very slowly and unevenly through test equipment. It, therefore, takes a long time to reach steady state conditions when water vapor transmission is directly measured. Accuracy and reproducibility is also effected for the same reason. Additionally, it has been found by mass spectrometer analysis that the third type of device described above does not always absorb all of the water vapor transmitted through a test sample and is relatively slow in reaching steady state conditions.

SUMMARY

In general, the present invention provides a cell used in an apparatus for rapidly and simply measuring the water vapor transmission rate through plastic films or like structures. The cell can also be used to determine the water content of solid, liquid and gaseous materials. The cell is adapted for absorbing and electrolyzing the water vapor transmitted through or from a test sample. The cell is designed so that simultaneous absorption and electrolysis of the water vapor takes place as near the test sample as possible, thus minimizing the transport delay and accuracy problems associated with water's highly polar molecule.

The cell has a hollow body with a removable closure and defines an interior space into which a test sample is placed. The interior space is disposed adjacent to the closure. If the transmission rate through a film sample is being determined, it is necessary to provide means for sealing the peripheral edge thereof to insure that the results include only the water vapor permeating through the sample. If the water content of a sample is being determined, it is necessary only to place the sample in the interior space.

An electrolysis assembly is disposed adjacent to the interior space. The assembly comprises a first electrode support and a first electrode and a second electrode support and a second electrode with a foraminous matrix having an electrically conductive water absorption material therein disposed electrically between the first and second electrodes. The electrodes are adapted for connection with an electrical power source which may provide either an alternating or direct current but preferably provides direct current. The minimum operable voltage for the power source is two volts, the decomposition voltage for water, but preferably is at least ten to twenty times higher during normal operation.

The cell is provided with means for passing the water vapor permeating through, or from the sample in the case of determining water content, from the interior space into the foraminous matrix which is preferably at least one passageway providing open communication therebetween. The cell also has means for passing oxygen and hydrogen generated by electrolysis of the water vapor in the foraminous matrix to the exterior of said cell which is preferably at least one elongated hollow providing open communication between the foraminous matrix and the exterior of the cell.

A controlled environment in the cell is achieved by placing the cell in an insulated enclosure and providing a regulated heating means within the enclosure. Environmental control within the cell during determination of the water vapor transmission rate through a sample also requires the inclusion of means for passing a quantity of water into the interior space to provide the desired relative humidity therein.

During operation of the cell, water vapor transmitted through or from the test sample passes from the interior space into the foraminous matrix where it is absorbed and electrolyzed. The oxygen and hydrogen generated by electrolysis then passes from the foraminous matrix to the exterior of the cell. The water vapor transmission rate or water content can be determined by two methods. In the first method, the water vapor transmitted through the cell is determined by a quantitative mass spectrometer analysis of the oxygen and hydrogen generated during electrolysis of the water vapor. When a mass spectrometer is used with the cell, it is not only possible to determine the water vapor transmission rate or water content of a sample but the cell may also be used to determine the transmission rate of gases such as oxygen, nitrogen and carbon dioxide through a sample. The second method is to measure the current needed to electrolyze the water vapor. The transmission rate or content of the water vapor can then be determined since it is related with primary accuracy to the electrolysis current flow through the cell. In accordance with Faraday's law, the electrolysis of 9.01 grams of water requires 96,500 coulombs. There is a small stable background current in the cell when it is dry which must be substracted from the total current if very accurate measurements are desired.

The cell body can be made from either a non-conductive material such as glass or a conductive material such as brass. However, it is necessary to electrically insulate the electrodes from each other if a conductive material is used.

An object of the present invention is to provide a cell that can be used in an apparatus for measuring water vapor transmission rate or water content of a test sample. Another object of the present invention is to provide a cell that will absorb and electrolysis water vapor from a test sample. A futher object of the invention is to provide a cell that is useful for determining very rapid and accurate measurements of water vapor transmission rate or water content. Other objects will be apparent from the following description and claims, reference being had to the accompanying drawings, forming a part of this specification.

BRIEF DESCRIPTION OF THE DRAWINGS

Preferred embodiments of the invention are shown in the drawings wherein:

FIG. 1 is a plan view of a cell in accordance with the invention;

FIG. 2 is a side elevation of a cell in accordance with the invention viewed from the bottom of FIG. 1;

FIG. 3 is an exploded cross section of a cell taken along line 3—3 in FIG. 1;

DESCRIPTION OF THE PREFERRED EMBODIMENTS

Figure 4:
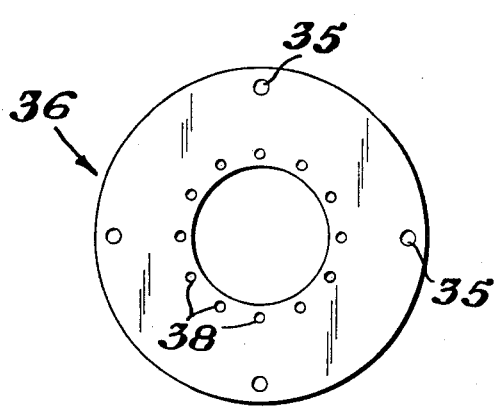
FIG. 4 is a reverse plan or bottom view of the first electrode support of a cell showing the water vapor passageways therethrough.

The following description illustrates the manner in which the principles of the invention are applied but are not to be construed as limiting the scope of the invention.

More specifically referring to FIGS. 1-3, a cell 10 for absorbing and electrolyzing water vapor from a test sample 32 comprises a hollow body 12 with a side wall 16 and a bottm wall 18 and a closure 14. Except as hereinafter noted, the cell 10 is entirely made of brass. Closure 14 can be securely sealed to the hollow body 12 by a rubber "0" ring 28, shown in FIG. 3. Closure 14 has a silicon rubber septum 26 through which a quantity of water may be passed into the interior space 23 without opening said space to the outside atmosphere. Closure 14 also has an elongated hollow 22 providing open communication between the interior space 23 and the exterior of cell 10. The hollow body 12 has two elongated hollows 20 and 24 providing open communication to the exterior of cell 10. The function and internal placement of the elongated hollows 20, 22 and 24 will be described later in detail.

Figure 5:
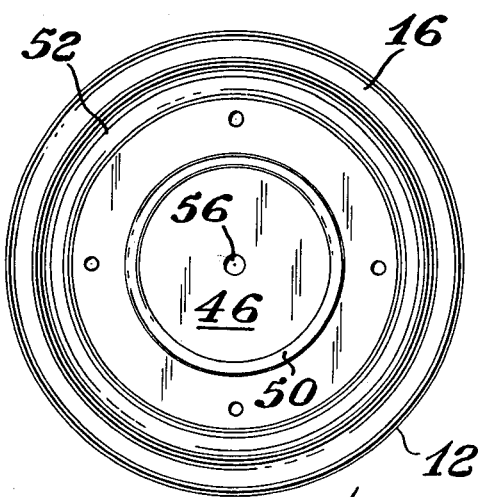
FIG. 5 is a plan of the hollow body of a cell without the electrolysis assembly showing the interior location of an elongated hollow providing open communication with the exterior of the cell.

Referring now to FIGS. 3-5, the internal elements of cell 10 will be described. A test sample 32, on which the water vapor transmission rate is to be determined, is placed in internal space 23 on a sample support 33 of fibrous polyethylene. In order to insure results indicating only water vapor permeation through the test sample 32, the outer edge thereof is sealed again on electrolysis assembly with a rubber "0" ring 30. The electrolysis assembly, in which electrolysis of the water vapor passing through the sample 32 takes place, comprises a first electrode support 36, a first electrode 40, a glass fiber body 42 impregnated with partially hydrated phosphorus pentoxide, a second electrode 46 and a second electrode support which is the bottom wall 18 of the hollow body 12. The electrolysis assembly is securely fixed within cell 10 by nylon screws 34 which pass through holes 35 in the first electrode support 36 and fasten into the bottom wall 18 of the hollow body 12. The rubber "0" ring 50 separates the first electrode support 36 from the bottom wall 18 and sealably closes off the interior of the electrolysis assembly from a gourd vacuum region or space 52 which is connected to the elongated hollow 24.

The electrode 40 and 46 are made from two mil thick platinum foil and are soft soldered or otherwise secured to the electrode supports 18 and 36, respectively. The use of platinum in electrodes 40 and 46 effectively prevents the electrolysis of the brass cell 10 during operation. The first electrode support 36 has a plurality of small pasageways 38, as more clearly shown in FIG. 4, positioned adjacent the outer edge of electrode 40 which will allow the water vapor permeating the test sample 32 to pass into the glass fiber body 42 through its outer edge. The glass fiber body 42 and the second electrode 46 also have centrally positioned holes 44 and 48, respectively, which will allow the oxygen and hydrogen generated during electrolysis of the water vapor in the glass fiber body 42 to pass through hole 56 of the bottom wall 18 and into the elongated hollow 20 leading to the exterior of cell 10. The guard vacuum region or space 52 is provided so that a vacuum can be drawn therein to effect a tight seal of "0" ring 28 between the closure 14 and the hollow body 12 and "0" ring 30 around the peripheral edge of the test sample 32. "0" rings 28, 30 and 50 also effectively insulate electrodes 40 and 46 electrically from each other which is necessary to prevent a short circuit within the brass cell 10.

The most crucial part of cell 10 involves the correct preparation of the glass fiber body 42. A disk of glass fibers about 20 mils in thickness is first prepared with the center hole 44. Three or four drops of a mixture of one part concentrated phosphorus acid to five parts acetone are placed on the interior of the disk away from its peripheral edge. The prepared glass fiber body 42 is air dried to remove the acetone. The glass filter body 42 is then placed in the cell 10 between the electrodes 40 and 46 and the voltage of a direct current power source connecting the electrodes 40 and 46 is adusted so the current passing between the electrodes does not exceed 30 milliamps. When the glass fiber body 42 has dried down, a full operating voltage of thirty volts should be applied to the cell 10. During the drying period, the phosphoric acid is converted to partially hydrated phosphorus pentoxide of about 88.0 percent which is supported by a glass fibrous matrix.

Although not shown in the drawings, cell 10 is placed in thermally insulated enclosure to control the environment therein during operation. A 75 watt tungsten lamp controlled by a thermoswitch is placed in the enclosure to maintain the temperature therein at 100° F. Also the elongated hollows 20, 22 and 24 are connected to a two-stage mechanical vacuum pump to control the atmosphere within cell 10 and facilitate operation thereof. The function of the vacuum pump can best be understood in relation to the cell operating procedure hereinafter described.

Figure 6:
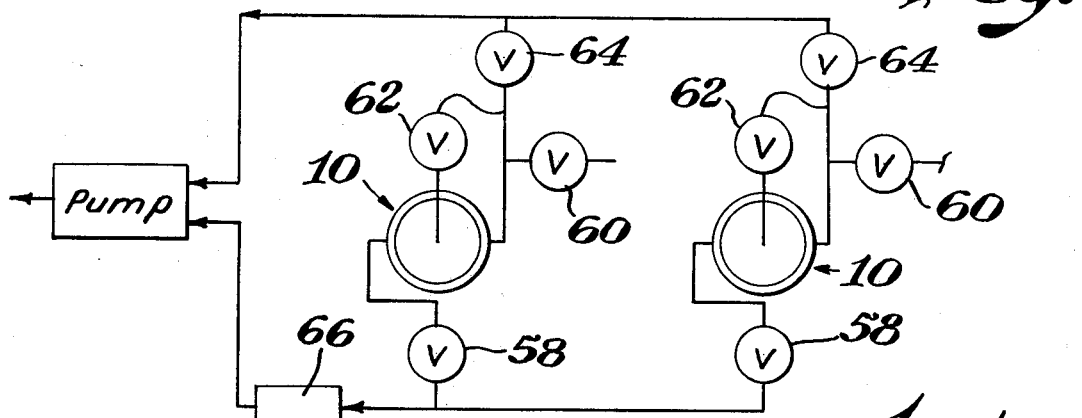
FIG. 6 is a schematic representation of a vacuum system used in conjunction with two cells.

Generally during operation of cell 10, water vapor permeating the test sample 32 passes through the sample support 33, the peripheral holes 38 and then laterally into the glass fiber body 42 where it is absorbed and electrolyzed into oxygen and hydrogen. The oxygen and hydrogen then pass through holes 44, 48 and 56 into the elongated hollow 20 which transports them to the exterior of cell 10. More specifically referring to FIG. 6, the operation of cell 10 can be described as follows. A test sample 32 is first placed in the interior space 23 on the sample support 33. With the closure 14 in place on the hollow body 12, the electrolysis assembly is evacuated by the first stage of the vacuum pump through valve 58 and elongated hollow 20 to remove any moisture picked up while placing the sample 32 into the cell 10. The interior space 23 and the gourd region or space 52 are then evacuated by the second stage of the vacuum pump through valves 62 and 64 and elongated hollows 22 and 24, respectively. The vacuum drawn within the cell is equivalent to about 2 mm. of mercury. After about two minutes valve 62 is closed and 10 microliters of water are injected through the silicon rubber septum 26 into the interior space 23 which gives 100 percent relative humidity on the top side of the test sample 32 and zero percent on the bottom side. After the electrolysis current has reached steady state conditions, the water vapor transmission rate of the test sample 32 can be determined directly from the current needed to electrolyze the water vapor or by quantitative measurements of the oxygen and hydrogen drawn away from cell 10 through the elongated hollow 20 to a mass spectrometer, as shown at 66 in FIG. 6. To remove the test sample 32 from cell 10 valves 58 and 64 are closed and valves 62 and 60 are opened to vent cell 10.

Figure 7:
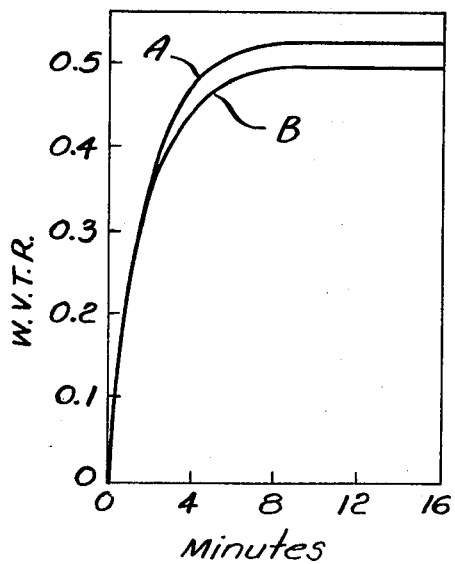
FIG. 7 is a graph showing the responsive time needed to obtain steady state water vapor transmission rate determinations using a cell in accordance with the invention.

FIG. 7 shows the response time for two films A and B when cell 10 is used to determine their water vapor transmission rates. A is a ½ mil thick saran film and B is a 2 mil thick polyethylene film. The following Table I illustrates the transmission rates of three films having a wide range and compares the present invention with a commercially available device.

Table I

| Sample | $t^1$ | Commercial Device[2] | Cell 10[3] |
|---|---|---|---|
| 1. Polystyrene film | 1 | 7.60 | 7.98 |
| 2. saran film | 1 | 0.20 | 0.223 |
| 3. laminated film (4 mils polyethylene/ 1 mil polyfluorocarbon) | 5 | 0.018 | 0.015 |

[1]thickness in mils
[2]test conditions of 100° F., 100% relative humidity on one side of sample & 10% relative humidity on the other
[3]calculated from electrolysis current at 100° F., 100% relative humidity one side of sample and 0% relative humidity on the other The maximum sensitivity of cell 10 is 0.0005

$$\frac{\text{gms-H}_2\text{O}}{100 \text{ in}^2\text{-day}}.$$

To obtain very accurate readings of water vapor transmission rate a stable back current of about 10 microamps in cell 10, equivalent ot 0.0053

$$\frac{\text{gms-H}_2\text{O}}{100 \text{ in}^2\text{-day}},$$

must be substracted from the total current. A very conservative dynamic range for cell 10 is 0.002 to 15.0

$$\frac{\text{gms-H}_2\text{O}}{100 \text{ in}^2\text{-day}},$$

Thus while certain representative embodiments and details have been shown for the purpose of illustrating the invention it will be apparent to those skilled in the art that various changes and modifications can be made therein without departing from the spirit and scope of the invention.

What is claimed is:

1. A method for determining water vapor transmission rate through a plastic film sample or like sample structure comprising:
   a. placing the sample in a sealed cell;
   b. evacuating substantially all water vapor from the sample and cell;
   c. introducing a measured quantity of water into the cell on one side of the sample;
   d. drawing the water vapor of such water through the sample and into a fibrous body having an electrically conductive water absorption material therein;
   e. electrolyzing the water vapor in the fibrous body into hydrogen and oxygen;
   f. transporting said hydrogen and oxygen from said cell to a mass spectrometer;
   g. measuring the quantity of said hydrogen and oxygen transported from said cell in said mass spectrometer; and
   h. determining the water vapor transmission rate of said test sample from the quantity of said hydrogen and oxygen transported.

2. The method of claim 1 wherein the transporting of said hydrogen and oxygen from said cell to said mass spectrometer is through a vacuum system.

3. The method in claim 1 wherein the fibrous body is formed from glass fibers which have been treated with a mixture of concentrated phosphoric acid and acetone and air dried to remove the acetone.

4. The method of claim 3 wherein the drying is sufficient to convert the phosphoric acid to partially hydrated phosphorus pentoxide of about 88 per cent which is supported by the glass fibrous matrix in the fibrous body.

* * * * *

UNITED STATES PATENT AND TRADEMARK OFFICE
CERTIFICATE OF CORRECTION

PATENT NO. : 4,050,995
DATED : September 27, 1977
INVENTOR(S) : Roger L. Bredeweg It is certified that error appears in the above-identified patent and that said Letters Patent are hereby corrected as shown below:

On the cover page, under Related U. S. Application Data, 1st line, delete Ser. No. "11,557" and insert --111,557--.

On the cover page, under Abstract, lines 9 and 10, delete "formaminous" and insert --foraminous--.

Column 1, line 41, change "surround" to --surrounding--.

Column 1, line 42, change "in" to --is--.

Column 3, line 28, change "substracted" to --subtracted--.

Column 3, line 40, change "futher" to --further--.

Column 4, line 13, change "bottm" to --bottom--.

Column 4, line 30, insert the word --the-- before "internal".

Column 4, line 47, change "gourd" to --guard--.

Column 4, line 50, change "electrode" to --electrodes--.

UNITED STATES PATENT AND TRADEMARK OFFICE
CERTIFICATE OF CORRECTION

PATENT NO. : 4,050,995
DATED : September 27, 1977
INVENTOR(S) : Roger L. Bredeweg It is certified that error appears in the above-identified patent and that said Letters Patent are hereby corrected as shown below:

Column 5, line 16, change "adusted" to --adjusted--.

Column 5, line 50, change "gourd" to --guard--.

Column 6, line 21, after "0.0005" insert the formula $\frac{gms-H_2O}{100\ in^2-day}$ as part of the sentence.

Column 6, line 28, after 0.0053 insert the formula $--\frac{gms-H_2O}{100\ in^2-day}--$ as part of the sentence.

Column 6, line 35, after 15.0, insert the formula $--\frac{gms-H_2O}{100\ in^2-day}--$ as part of the sentence.

Column 6, line 28, change "ot" to --to--.

Signed and Sealed this

Twenty-eighth Day of February 1978

[SEAL]

Attest:

RUTH C. MASON
Attesting Officer

LUTRELLE F. PARKER
Acting Commissioner of Patents and Trademarks